United States Patent
Bischoff et al.

(10) Patent No.: US 8,597,283 B2
(45) Date of Patent: Dec. 3, 2013

(54) OPHTHALMOLOGIC LASER SYSTEM AND OPERATING METHOD

(75) Inventors: Mark Bischoff, Jena (DE); Manfred Dick, Gefell (DE); Juergen Ledermann, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 130 days.

(21) Appl. No.: 12/996,255

(22) PCT Filed: Nov. 4, 2009

(86) PCT No.: PCT/EP2009/007892
§ 371 (c)(1),
(2), (4) Date: Dec. 3, 2010

(87) PCT Pub. No.: WO2010/051975
PCT Pub. Date: May 14, 2010

(65) Prior Publication Data
US 2011/0224658 A1    Sep. 15, 2011

(30) Foreign Application Priority Data
Nov. 6, 2008  (DE) .................. 10 2008 056 488

(51) Int. Cl.
*A61F 9/01*  (2006.01)
*A61B 3/10*  (2006.01)

(52) U.S. Cl.
USPC ........ 606/5; 606/4; 606/6; 606/107; 351/215; 351/221

(58) Field of Classification Search
USPC ........................................ 606/4, 5, 107, 166
See application file for complete search history.

(56) References Cited

U.S. PATENT DOCUMENTS

| | | | |
|---|---|---|---|
| 3,013,467 A | 12/1961 | Minsky | |
| 5,092,863 A | 3/1992 | Schanzlin | |
| 5,672,881 A * | 9/1997 | Striepeke et al. | 250/461.2 |
| 6,125,294 A | 9/2000 | Scholl et al. | |
| 6,585,723 B1 * | 7/2003 | Sumiya | 606/5 |
| 6,736,508 B2 * | 5/2004 | Xie et al. | 351/209 |
| 2004/0207811 A1 * | 10/2004 | Elsner | 351/205 |
| 2006/0084956 A1 * | 4/2006 | Sumiya | 606/12 |
| 2006/0155265 A1 | 7/2006 | Juhasz et al. | |
| 2006/0228008 A1 | 10/2006 | Dioguardi et al. | |
| 2008/0319464 A1 * | 12/2008 | Bischoff et al. | 606/166 |

FOREIGN PATENT DOCUMENTS

| | | | |
|---|---|---|---|
| DE | 102 07 535 A1 | 9/2003 | |
| DE | 10 2005 030 347 A1 | 1/2007 | |
| EP | 0983757 A2 * | 3/2000 | A61F 9/01 |
| EP | 1 806 116 A1 | 7/2007 | |
| WO | WO 2006/051364 A1 | 5/2006 | |
| WO | WO 2008/064771 A1 | 6/2008 | |
| WO | WO 2009/146906 A2 | 12/2009 | |

* cited by examiner

*Primary Examiner* — Sam Yao
*Assistant Examiner* — Boniface N Nganga
(74) *Attorney, Agent, or Firm* — Patterson Thuente Pedersen, P.A.

(57) ABSTRACT

An ophthalmologic laser system and an operating method. The laser system includes a laser, a scanner unit, a focusing lens and a beam splitter that directs radiation that reaches the beam splitter from the direction of the area of examination through a confocal aperture orifice onto a detector. The invention also includes a control unit with which a cornea arranged in the examination area can be irradiated by the laser at illumination laser power and detection light can be registered by the detector. The cornea is scanned in three dimensions, in that the cornea is irradiated at multiple points and detection light is registered from there. Based on the detection light, a laser cut in the cornea is identified and the form and/or position of the laser cut calculated. The invention further relates to refractive laser surgery.

21 Claims, 4 Drawing Sheets

OPHTHALMOLOGIC LASER SYSTEM AND OPERATING METHOD

PRIORITY CLAIM

The present application is a National Phase entry of PCT Application No. PCT/EP2009/007892, filed Nov. 4, 2009, which claims priority from German Application Number 102008056488.5, filed Nov. 6, 2008, the disclosures of which are hereby incorporated by reference herein in their entirety.

FIELD OF THE INVENTION

The invention relates to an ophthalmological laser system, particularly for the purpose of a surgical follow-up treatment of the cornea, with a laser, the radiation of which is focusable in an examination region as illumination light via an illumination beam path, which includes a scanner unit and focusing optics. Furthermore, the invention relates to an operating method for an ophthalmological laser system.

BACKGROUND

In ophthalmology it has been established, in case of defective vision, to form the cornea of the human eye with its approximate thickness of 500 μm through ablation of tissue in order to correct myopia, hypermetropia, and astigmatism. This is called refractive surgery. Nowadays it is executed either with mechanical means, such as microkeratomes in combination with laser radiation, or purely optically with laser radiation. Thereby, the laser radiation of the ArF excimer laser, the pulsed radiation of which exhibits a wavelength of 193 nm, has proven successful. With radiation of said wavelength, satisfactory ablation results with minimal, negligible side effects are achieved.

Thereto, two different methods for executing such an operation are known. With photorefractive keratectomy (PRK), the upper epithelium layer with an approximate thickness of 50 μm is irreversibly removed from Bowman's membrane with a surgical instrument called a hockey knife and the laser ablation is executed on the stromal surface. Within a healing process, a new epithelium forms on the laser-treated surface after surgery. However, this is associated with pain for the patient.

During laser-supported intrastromal keratomileusis (LASIK), a stromal flap with an approximate thickness of 160 μm is detached from the cornea by means of a mechanical microkeratome and folded back around a non-detached area similar to a hinge. Thereby, the flap is usually produced concentrically with the pupil. The laser treatment is executed in the intrastromal tissue. After treatment, the flap is folded back.

Thereby, the patients experience minimal pain after surgery and quick vision recovery. However, the procedure with a microkeratome is fraught with risk, and the remaining thickness of the cornea, available for the refractive correction, is less than with PRK.

Recently, strongly focused radiation from femtosecond lasers has been applied in order to execute incisions in the cornea (Femto-LASIK). Such devices are also called laser microkeratome. Thereby, a photodisruption is produced in the focus, which leads to a minimal formation of bubbles in the stromal tissue. If focal spot is set next to focal spot by means of a scanner system, random incisions (perforations) can be made in the cornea. Said incisions are hereinafter called laser incisions. For example, from US 2006/0155265 A1 (Intralase Corp.) it is known to cut the flap by means of a femtosecond laser system. The ablation of the stromal tissue, necessary for a refractive correction, is subsequently executed conservatively by means of an excimer laser, completely forgoing a mechanical treatment; however, two laser systems are required.

In WO 2008/064771 A1 (Carl Zeiss Meditec AG), a femtosecond laser system is described, which can also prepare the flap but is additionally capable of separating the ablation of stromal tissue, necessary for a refractive correction, through dual incisions for the preparation of a lenticle. This can be called femtosecond lenticle extraction (FLEx). Subsequently, the lenticle can be removed with a pair of pincers after opening the flap. As a result, only one laser system is required, the use of an excimer laser can be forgone.

In some cases of refractive laser correction of eyes, it might become necessary, due to mistreatment or changes of the refractive condition, to perform, in turn, a laser-supported follow-up treatment. Thereby, the flap in the stromal bed must frequently be mechanically slightly detached; as a rule, however, at the perimeter of the flap, epithelium has grown in dependence of the elapsed time since the preceding treatment. In order to perform follow-up treatment with as few complications as possible, the original points of incision should be reutilized as precisely as possible.

However, a mechanical repreparation of closely spaced incisions poses the risk of inadvertently removing additional or less tissue in comparison to an initial incision.

In principle, the repreparation of the flap is problematic since biomechanical changes after the initial laser treatment, particularly regression processes, might have altered the position of the incisions with regard to the front of the cornea, which serves as reference. As a result, complications due to an imprecise repreparation are virtually unavoidable during follow-up treatment if the aforementioned influences cannot be neglected for other reasons (for example, when the follow-up treatment is performed shortly after the initial treatment).

Said problem does not only occur during the repreparation of the flap but, under certain circumstances, also in the case of the femtosecond lenticle extraction during the actual refractive follow-up treatment if previous laser incisions are to be reutilized. If, for example, such a lenticle extraction is performed minimally invasive, i.e., the lenticle is removed through a small peripheral incision ("Small Incision Lenticle Extraction;" SMILE) without opening an entire flap, it might become necessary during follow-up treatment to prepare a complete peripheral opening for a flap following said peripheral incision, thereby leaving a hinge at the edge of a previously untreated peripheral area.

A further option for improving defective vision through laser surgery is known from WO 2006/051364 A1 (20/10 Perfect Vision Optische Geraete GmbH). With this method, incisions are executed with a femtosecond laser in the stromal tissue in order to create a continuous cavity, particularly in cylindrical form, without ablation of tissue. During the collapse of the cavity due to the intraocular pressure, the cornea relaxes and takes on a new form with altered curvature. In principle, radial keratotomy (Fjodorov), and astigmatic keratotomy are similar methods. With the appropriate placement of relaxing incisions, which can also be performed through laser surgery, defective vision can be improved.

However, with said method it is difficult to immediately recognize an incomplete treatment, a mistreatment, or an undercorrection or overcorrection. By contrast, during the Femto-LASIK method, e.g., a non-detaching flap due to insufficient incisions is immediately recognized, allowing for the initiation of an immediate follow-up treatment without complications. Therefore, one or several follow-up treatments might also be required with the aforementioned methods in order to iteratively achieve an improvement of the defective vision, for example. However, in the meantime, the biomechanical changes, as described above, can occur.

SUMMARY OF THE INVENTION

The invention is based on the task of improving an ophthalmological laser system and a corresponding operating method of the initially mentioned type in such a way that a follow-up treatment of the cornea after an initial laser-supported treatment is made possible with great accuracy.

The task is solved with an ophthalmological laser system, which exhibits the characteristics described herein, and with a method which exhibits the characteristics described herein. Advantageous embodiments of the invention are described in this application as well.

According to the invention, a beam splitter in the illumination beam path, and a control unit are provided, whereby radiation, which reaches the beam splitter from the direction of the examination region, arrives at a detector through a confocal aperture diaphragm, and whereby the control unit can irradiate a cornea positioned in the examination region by application of a laser at illumination laser power and map detection light by means of the detector, whereby it scans the cornea three-dimensionally through irradiating said cornea at several spots, maps detection light, identifies an existing laser incision in the cornea by means of the detection light and determines form and/or position of the laser incision.

The ophthalmological laser system, according to the invention, with integrated confocal measuring system, and the operating method, according to the invention, allow for the utilization of already existing incisions within the course of a repeat or follow-up treatment with great accuracy through the recognition of the actual position of already existing laser incisions from a previous femtosecond laser treatment or LASIK of the cornea. For example, the follow-up treatment can be exactly aligned to the initial incisions so that previous laser incisions can be recut or new incisions positioned with great accuracy relative to the existing laser incisions. Thereby, the localization of the laser incisions is only made possible through the confocal detection since the intensity of the light backscattered in the cornea is too low due to the inherent properties of the cornea—for a high imaging quality, the scattering must be as insignificant as possible. Only a confocal detection sufficiently suppresses stray light in such a way that the increased scattering at the initial incisions is detectable and usable for localization. Furthermore, the invention allows for an in-vivo pachymetry of the cornea so that layers of the cornea can be used as a reference system for orientation. The invention also allows for an intraoperative 3D representation of the cornea on a monitor for better orientation of the surgeon.

In an advantageous embodiment, the beam splitter is a polarization beam splitter, which decouples the detection light on the detector in such a way that it exhibits a polarization direction different from the emitted illumination light. A large portion of the light, which impinges on the beam splitter from the examination region, originates from reflections on the optical components of the beam path, e.g., the surfaces of the focusing optics; therefore, it exhibits the same polarization direction as the illumination light. Since the beam splitter only directs light as detection light to the detector with a different polarization direction, such stray light is suppressed. However, light backscattered in the cornea exhibits an altered polarization direction. Therefore, the detection of the light backscattered in the cornea is possible with greater accuracy.

It is possible to achieve an even greater signal strength, wherein an optical phase retardation system in the illumination beam path between the focusing optics and the examination region is arranged in such a way that the passing illumination light obtains a polarization direction corresponding to the decoupled detection light.

As a result, the stray light exhibits the same polarization direction as the radiation from the laser, while the illumination light, which reaches the cornea and is modified in the phase retardation system, obtains a defined, different polarization direction. Through the selection of the light of said polarization direction as detection light by means of the polarization beam splitter, only such light, which was backscattered in the cornea, is detected almost exclusively. Stray light, which originates from reflections on optical components, is even more effectively kept away from the detector.

Moreover, due to the polarization properties of the cornea, varying polarization properties of the introduced diagnostic radiation are advantageous for the image generation within varying areas of the cornea. Said properties can be produced through one or several polarizing optical elements in the illumination beam path.

Advantageously, a polarization filter is positioned in the detection beam path between the beam splitter and the detector, which is torsion-resistant or rotatable with regard to its polarization direction. With regard to its effect, a torsion-resistant polarization filter corresponds to the aforementioned polarization beam splitter. Due to the polarization properties of the cornea, a selection of the polarization direction backscattered to the confocal detector through a twist of the polarization filter assigned to the detector is advantageous for the efficient diagnosis of particular areas of the cornea. Hence, a complete detection of an overall image with high contrast of an initial incision in the cornea is accomplished through multiple scanning at various settings of the polarization filter to a respective individual image and appropriate superimposition of the individual images to the overall image. A polarization beam splitter can also be designed rotatable in order to selectively detect stray light of varying polarization directions. However, the detection of an initial incision is also possible with a torsion-resistant polarization filter/polarization beam splitter or entirely without polarization filtering, particularly by means of a single scan cycle. A single scan cycle can be executed in a short period of time.

In some embodiments, the radiation of the laser is, in addition to illumination laser power, adjustable to a surgical therapy laser power. As a result, the same laser can be utilized with great positioning accuracy for the illumination during determination of form and/or position of the laser incisions in the cornea as well as for the subsequent treatment.

Advantageously, the control unit, after determining form and/or position of the initial incisions in the cornea, determines the irradiation control data for a laser-supported surgical follow-up treatment while taking into account the determined form and/or position of the laser incisions and irradiates the cornea with surgical therapy laser power in accordance with the determined irradiation control data. As a result, the follow-up treatment is possible with great accuracy since the actual current position of the initial incisions allows for their reutilization or extension/continuation. Therefore, errors during the reutilization or extension/continuation of initial incisions due to a biomechanical change can be minimized.

Expediently, the control unit immobilizes an eye containing the cornea before irradiation with illumination laser power by application of an immobilization device and releases the immobilization after the determination of the form and/or position of the laser incisions or after surgical radiation treatment.

In order to improve the image contrast, a lock-in amplifier, coupled with the laser, can be provided for the detector. This allows for the mapping of the detector light with great sensitivity so that a possibly assigned treatment can be executed with great accuracy.

For the three-dimensional scanning of the cornea, the radiation exposure can be reduced in such a way that two consecutive scan points differ from each other in all three spatial coordinates. Through this type of scanning, a representative model of the cornea with regard to form and/or position of initial incisions can be obtained in a short period of time. A control of the scanners in the form of sine functions is technically particularly advantageous.

Controlling the x-y scanners in such a way that one of the scanners is controlled with exactly double the frequency than that of the other scanner results in a Lissajous figure, which resembles the figure 8.

In one example embodiment, a pulse frequency of the laser light, depending on the motion speed of a focal point of the laser beam relative to the corneas, is chosen. As a result, the radiation exposure of the cornea and the eye overall can be decreased during identification and detection of the initial incisions, and particularly during the follow-up treatment.

Advantageously, the step of irradiating and scanning the cornea can be executed several times along a scan curve, whereby the scan curve is utilized during each scan cycle in a varyingly offset and/or varyingly rotated position. Since a depth scan and a side scan through the confocal detection system only results in a sectional image of the cornea, an almost complete three-dimensional analysis of an initial incision is possible, for example, through repetition with a rotated scan curve in increments of 1°, 5°, 10°, . . . 90° centrally symmetrical to the first scanning cycle.

Expediently, a darkfield value is subtracted from the mapped detection light. This can either be a mutual darkfield value for all scan points or several point-specific darkfield values. This embodiment allows for a greater accuracy of the imaging of the light backscattered in the cornea.

In addition to the ophthalmological laser system and an operating method, the invention also comprises a computer program for said method as well as a control unit, which is designed for the execution of the operating method, according to the invention.

If initial incisions are the result of a minimally invasive treatment, such as SMILE, they can, by means of the invention and if so desired, be transformed into an incision geometry similar to the classic LASIK. Thereby, incisions already applied during the primary treatment, can be expanded.

For example, a primary incision, which was essentially applied at a constant distance to the front of the cornea, can be radially expanded in order to create more favorable conditions for a follow-up treatment. Expediently, the expansion is based on a previous identification and localization of the initial incision(s).

BRIEF DESCRIPTION OF THE DRAWINGS

In the following, the invention shall be further explained by means of embodiment examples.

In all drawings, all corresponding parts bear the same legend.

DETAILED DESCRIPTION

Figure 1:
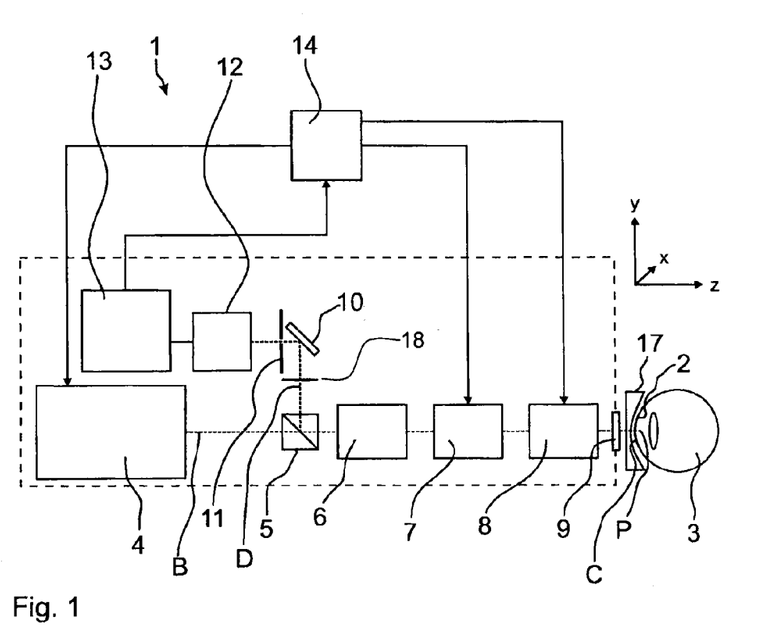
FIG. 1 depicts an ophthalmological laser system for the analysis of the cornea.

FIG. 1 shows an exemplary ophthalmological laser system 1 for identification and localization of an existing laser incision C in a cornea 2 of an eye 3. The laser system 1 comprises a laser 4, a polarization beam splitter 5, scan optics 6, a scanner unit 7, focusing optics 8, and an optical phase retardation system 9, which together form an illumination beam path B; as well as a deflection mirror 10, a confocal aperture diaphragm 11, and a detector 12, which form a decoupled detection beam path D. In addition, the laser system 1 comprises an amplifier 13 and a control unit 14. Between the laser system 1 and the eye 3, a contact glass 17 with an immobilization device for the eye 3 is positioned, behind which lies the examination region. Other embodiments for the realization of the solution, according to the invention, are possible (not depicted).

For example, the laser 4 is designed as pulsed TiSa infrared laser with a pulse length between 100 fs and 1000 fs. It emits laser radiation at an eye-safe illumination laser power in the range of 100 mW. The scanner unit 7 comprises, for example, a number of galvanometric mirrors for the deflection of the laser radiation in the x- and y-directions via the cornea 2. The focusing of the laser radiation in z-direction along the optical axis is effected, e.g., through a movable lens or lens group within the scan optics 6 or the focusing optics 8, or alternatively through a movable tube lens (not depicted). The optical phase retardation system 9, for example, is designed as $\lambda/4$ plate, which forms a border of the laser system. The detector 12, e.g., is designed as photomultiplier (PMT) or as avalanche photo diode (APD) since the light intensities to be mapped are low. The amplifier 13 is designed as lock-in amplifier and connected to the detector 12 as well as the laser 4.

The pulsed IR laser radiation emerges from the laser 4 and initially passes unchanged through the polarization beam splitter 5. Then it is focused via scan optics 6, scanner unit 7, and focusing optics 8 as illumination light on a scan point P in the cornea 2. Said scan point P can be shifted in the cornea 2 by means of the scanner unit 7 and a movable lens or lens group within the scan optics 6 or the focusing optics 8 in x-, y-, or z-direction. Thereby, the optical phase retardation system 9 effects a defined change of the polarization direction of the illumination light passing through.

At the boundary layers and inside the cornea 2, a scattering/reflection of the IR radiation occurs, whereby the radiation is partially depolarized. Backscattered/reflected light also impinges on the illumination beam path B and there returns all the way back to the polarization beam splitter 5. The radiation components with unchanged polarization status pass through the polarization beam splitter 5 onto the laser 4. This refers particularly to reflections which originate from the scan optics 6 or the focusing optics 8.

Such radiation components, which, after passing through the phase retardation system 9 and/or through depolarization in the eye 3, exhibit a changed polarization status in the cornea 2, are deflected by the polarization beam splitter 5 as detection light into the detection beam path D to the detector 12. The detection light passes via a deflection mirror 10 through the confocal aperture diaphragm 11 onto the detector 12. In an alternative embodiment (not depicted), the deflection mirror 10 can be omitted or replaced by other beam guidance units. The confocal aperture 11 acts as discriminator in the z-direction, therefore, spatially resolved, only backscattered light is detected from a low focus volume. The control unit 14, through the deflection of the illumination light in x- and y-direction by means of the scanner unit 7 and change of the focusing in z-direction by means of the focusing optics 8, can irradiate random scan points P inside of the cornea 2 with illumination light and determine the strength of the backscatter at said points P via the intensity of the corresponding detection light.

In order to determine information about existence as well as form and position of initial incisions in the cornea 2 with great accuracy in a short period of time, a suitable spatial distribution of points P is scanned. From the hereby obtained values for the intensity of the backscatter, form and position of the initial incisions can be reconstructed since the backscatter at the boundary layers of and within the initial incisions is intensified when compared to the untreated cornea. As a result, a follow-up treatment can be performed patient-specific while taking the initial incisions into account.

In the depicted embodiment, the optical phase retardation system 9 between the eye 3 and focusing optics 8 effects a defined rotation of the polarization direction of the passing illumination light, while stray light, previously reflected at the optical components, maintains the original polarization direction. As a result, the relative intensity of the detection light is increased since the polarization beam splitter 5 separates only light with deviating polarization direction as detection light. In alternative embodiments (not depicted), the optical phase retardation system 9 can be omitted. Alternatively or additionally, additional polarizers (not depicted) can be positioned in the illumination and/or detection beam path in order to improve the signal quality. For example, a polarization filter 18 is positioned in the detection beam path between the beam splitter and the detector, which is torsion-resistant or rotatable with regard to its polarization direction.

In another embodiment, the phase retardation system can be realized as depolarizer so that the extent of the phase retardation varies via the beam profile.

Since the signals registered at the detector 12 exhibit a very low intensity, the electronic amplifier is adjusted to an optimized signal-to-noise ratio. A particularly advantageous embodiment is the lock-in amplifier, which is temporally synchronized with the pulse generation and/or the repetition frequency of the laser 2. Other embodiments, for example, utilize so-called boxcar techniques or scanning techniques (sampling) with adding up or averaging for noise suppression. Advantageously, the entire amplifier system of the detector signal exhibits a nonlinear characteristic. However, a peak detector and/or a sample-and-hold circuit can also be used to achieve signal improvement.

Figure 2A:
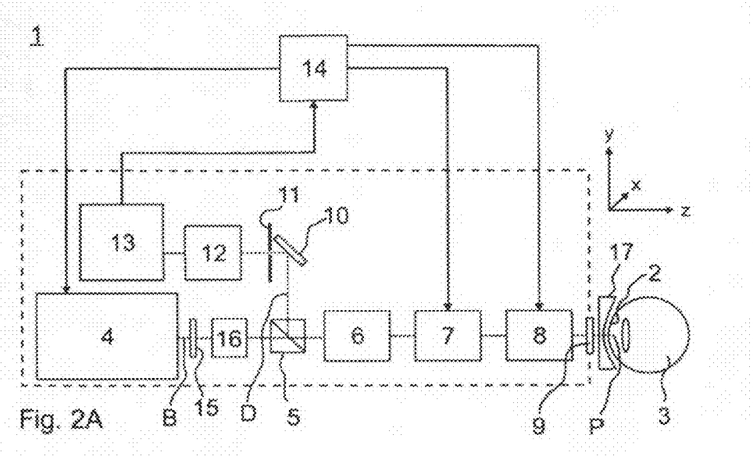
FIGS. 2A and 2B depict ophthalmological laser systems for the analysis and treatment of the cornea.
Figure 2B:
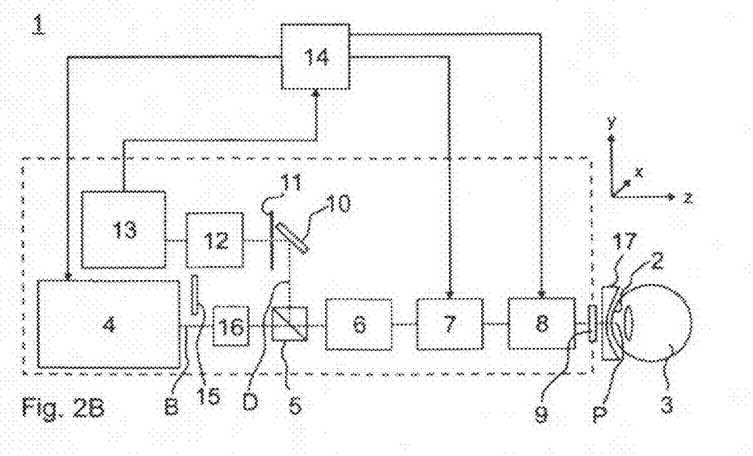

FIGS. 2A and 2B depict an ophthalmological laser system 1 for combined identification of initial incisions of an initial treatment and execution of a laser-supported follow-up treatment. It corresponds to a large extent with the laser system 1 in accordance with FIG. 1 but is additionally equipped with an attenuator 15, which can be tilted into the illumination beam path B, and a modulator 16, e.g., an acousto-optical modulator. The attenuator 15 is used for switching between an illumination laser power and therapy laser power. Illumination laser power is obtained through the attenuator 15, tilted into the illumination beam path B, and therapy laser power is obtained without the attenuator 15. The optical components, particularly optics 6 and 8, are optimized, corrected, and synchronized towards the goal of a best possible focus miniaturization. For example, its optical aberrations are minimized to a high degree, requiring only a low energy input for a photodisruption.

Figure 3:
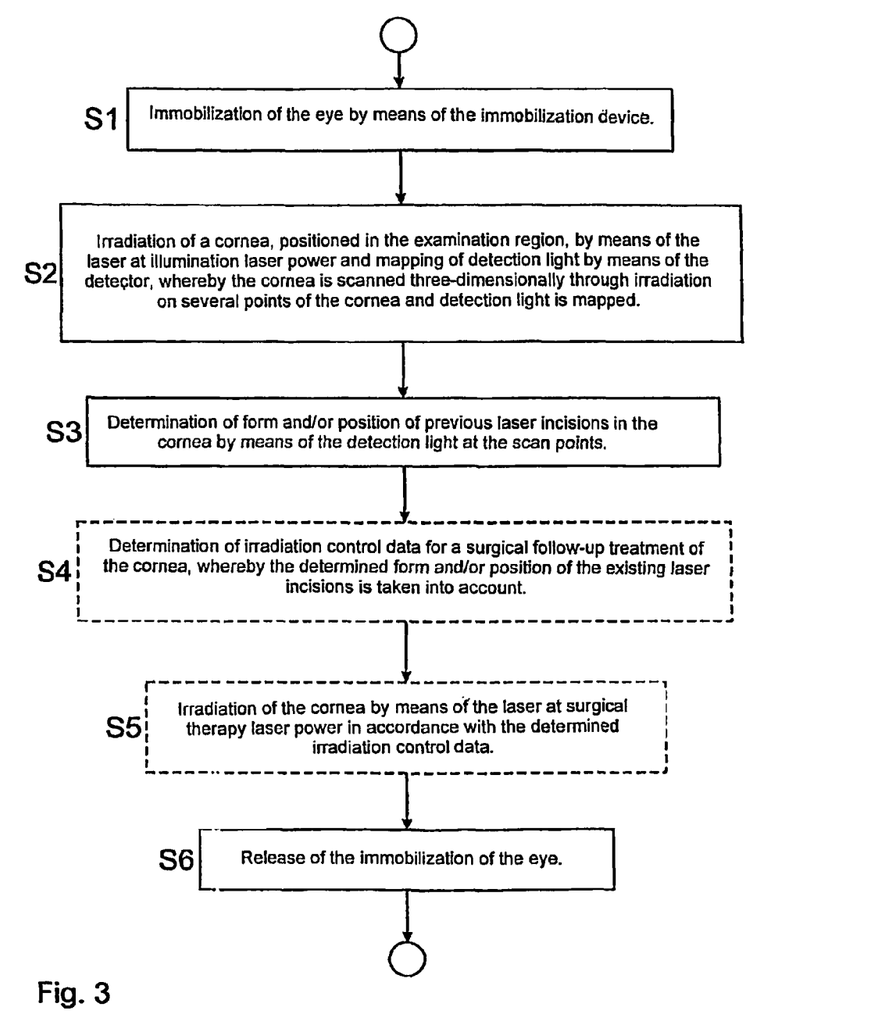
FIG. 3 is a flow diagram of an operating method.

The control unit 14 executes the operating method as shown in FIG. 3, whereby for a pure detection of initial incisions in the cornea 2 only the solidly outlined steps S1, S2, S3, and S6 are executed.

For a follow-up treatment all steps are executed. Thereby, the laser 4 is utilized not only for illumination during the detection phase but also for the treatment of the cornea 2 during the immediately following treatment phase.

At first, the eye 3 of the patient is immobilized, for example, drawn towards a contact glass device by means of a vacuum (step S1). In addition, the head of the patient can also be immobilized. Through a suitable target, the eye position of the patient can be kept as constant as possible. Thereby, an adjustable compensation of the angle between geometry and optical axis of the eye 3 is possible.

The illumination light at illumination laser power is guided across the cornea 2 along an adjustable, continuous, three-dimensional scan curve or scan structure, and detection light is mapped (step S2). Thereby, the pulse frequency, in dependence of the speed of the scan movement, is adjusted in such a way that a lower pulse frequency results from a slow scan movement than from a fast scan movement. The backscattered detection light is assigned sectionally or pointwise to individual points of the scan curve. Due to the consistency of the scan curve, consecutive scan points differ with regard to all spatial coordinates. From the detected signal values, respective darkfield values are advantageously subtracted, which are determined in a separate calibration phase.

From the intensities assigned to the scan points, initial incisions are identified and their form and position reconstructed (step S3). Thereto, scan points, e.g., the intensity of which exceeds an intensity threshold, which is predetermined or specified by the surgeon, are determined as sampling points of the initial incision. With an adjustment calculation, a model of the initial incision, either assumed or known from the previous treatment, is adjusted to the three-dimensional coordinates of the determined sampling points of the initial incision in order to make available all coordinates of the initial incision as a basis for the surgical follow-up treatment of the initial incision. Said information is used to adjust the incisions to be performed, e.g., predefined by the operator beforehand, to the actual individual condition of the cornea 2 before the irradiation control data are determined (step S4).

The irradiation control data comprise, e.g., control signals for the axes of the scanner unit 7 and/or the internal z-focusing, and for the laser beam source and the power modulator 16. If the incision geometries produced during the initial treatment are known, only reduced information about the already implemented incisions might sometimes be required in order to reconstruct the entire position of the incisions. If, for example, only the centering of a flap incision is doubtful, even the determination of two peripheral incision points within the reference system provided by the contact glass will suffice.

Immediately thereafter, by means of the irradiation control data, the surgical follow-up treatment is executed with therapy laser power (step S5). Advantageously, pulse energies from 10 nJ to 3 µJ, particularly 50 nJ to 1 µJ, are utilized. Thereby, for example, one or several series of photodisruptions are produced through the laser radiation at a pulse frequency from 100 kHz to 10 MHz and with a pulse length of less than 1 ps, particularly from 100 fs to 800 fs. Lastly, the immobilization of the eye 3 is released (step S6).

Due to the identical beam path for analysis and treatment, the system 1 is self-calibrating. Since the irradiation control data are determined by means of the information about form and/or position of the initial incisions in the cornea, obtained with the identical beam path, the treatment always allows for great accuracy.

Through the use of adjusted scan curves (scan patterns), for example, in the form of Lissajous figures, the combined procedure can also be executed in a short period of time, for example, within a maximum of 30 seconds, which reduces inaccuracies due to movement and leads to better acceptance by the patient.

Figure 4:
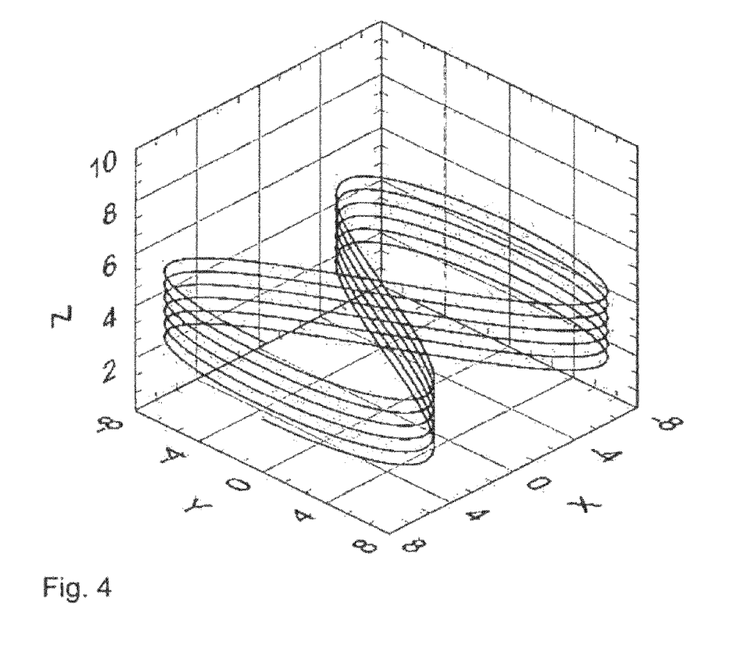
FIG. 4 is a space curve for the scanning of the cornea.

FIG. 4 shows an exemplary scan curve in the form of spatially offset figures 8, which can be realized as a Lissajous figure by means of the scanner unit 6. It has the advantage of allowing for the determination of the data of existing laser incisions with great accuracy in a short period of time.

Other exemplary forms of scanning and/or rastering can be (not depicted): two crossed rectangles in space; two cylindrical surfaces; a cylindrical body with a profile in the form of a figure 8 or 4; several scans along one-dimensional lines. It is also possible to raster the volume of a cylinder or a cube. The volumes and/or surfaces can be scanned continuously or only partially, i.e., with gaps between the individual scan points. As a result, greater distances can occur between individual lines.

In the following, two exemplary cases of applications of the invention are described.

EXAMPLE 1

For example, after a correction of the refractive power of the cornea was performed with the LASIK method on a patient within the last few days or even several years, whereby the flap was produced with a femtosecond laser system and the actual refractive correction was performed with an excimer laser (Femto-LASIK), a laser-based follow-up correction, e.g., with the femtosecond lenticle extraction method is now to be performed. For said purpose, the patient's eye 3 is coupled with the femtosecond laser therapy device 1. Preferably, this is effected centered to the optical axis of the therapy system 1. Then the method as described above is performed with the confocal detector 11/12 in such a way that the form and position of the previous flap cutting plane are determined with regard to the contact glass 17, firmly coupled with the eye to be treated. Thereto, two preferably orthogonal sectional images of the cornea 2 to be treated are produced, which intersect on the optical axis of the laser beam. With or without the utilization of other information, the form and position of the previous flap cutting plane is, within the course of the follow-up treatment, retreated with a secondary flap incision positioned at the same depth.

Thereby, it is advantageous but not mandatory for the lateral extension of the flap cutting plane to reach or exceed the initial extent.

Part of the previous peripheral incision should be retreated with a secondary peripheral incision. However, sometimes it is better not to align the secondary opening incision with the initial peripheral incision, e.g., with a small treatment diameter as would be applicable for the femtosecond lenticle extraction method. In any case, it is easily possible for the surgeon to once again manually sever the initial cutting planes.

The secondary peripheral incision and the secondary flap cutting plane do not have to be centered to one another.

In addition to the secondary flap cutting plane, the lenticle cutting plane is also produced, which together with the secondary flap cutting plane encases a lenticle, and the extraction of which effects the desired change of the refractive power of the cornea during the course of the follow-up treatment. With the concluding manual extraction of the lenticle, the refractive power of the cornea changes in the desired fashion.

EXAMPLE 2

At first, the position of the initial incisions are determined with regard to the contact glass 17 during the follow-up treatment (see Example 1). However, since the target of the follow-up correction, e.g., is only a slight change in the refractive power of the cornea 2, e.g., up to 2 dpt, only relaxing incisions without ablation are executed instead of a femtosecond lenticle extraction. A manual extraction of tissue is not scheduled. According to the invention, the information about the position of the initial cutting planes is used to calculate new cutting planes which effect a change in the refractive power of the cornea 2 through the change of the form of the front of the cornea 2. Form and position of said cutting planes can, for example, be determined via a finite element method (FEM) or from experience.

The follow-up treatment method is not only suited for limiting the change of the amplitude of the refractive power (low correction amount) but also for limiting the optical zone, e.g., for producing a bifocal system for pseudo-presbyopia correction.

LEGEND

1 Ophthalmological laser system
2 Cornea
3 Eye
4 Laser
5 Polarization beam splitter
6 Scan optics
7 Scanner unit
8 Focusing optics
9 Optical phase retardation system
10 Deflection mirror
11 Confocal aperture diaphragm
12 Detector
13 Amplifier
14 Control unit
15 Attenuator
16 Modulator
17 Contact glass
B Illumination beam path
D Detection beam path
P Scan point
C Laser incision

The invention claimed is:

1. An ophthalmological laser system, for the purpose of a surgical follow-up treatment of a cornea, comprising:
   a laser, emitting radiation that is focusable in an examination region as illumination light via an illumination beam path, the illumination beam path including a scanner unit, and focusing optics;
   a beam splitter in the illumination beam path that directs radiation, which reaches the beam splitter from the direction of an examination region to a detector as detection light through a confocal aperture diaphragm, and a control unit programmed to execute the following:
   irradiating of the cornea positioned in the examination region by the laser at an illumination laser power and mapping of detection light by the detector, wherein the control unit causes scanning of the cornea three-dimensionally through irradiating said cornea on several points and mapping detection light;

identifying of an existing laser incision in the cornea from a previous femtosecond laser treatment and determination of form, position or both form and position of the existing laser incision by analysis of the detection light; and determining of irradiation control data for a refractive surgical follow-up treatment, wherein the control unit takes into account the determined form, position or both form and position of the laser incision.

2. The ophthalmological laser system, according to claim 1, wherein the beam splitter is a polarization beam splitter, which selectively decouples the detection light onto the detector such that the detection light exhibits a polarization direction different from the illumination light.

3. The ophthalmological laser system, according to claim 1, further comprising an optical phase retardation system positioned in the illumination beam path between the focusing optics and the examination region such that the illumination light passing through the optical phase retardation system is given a polarization direction which corresponds with the decoupled detection light.

4. The ophthalmological laser system, according to claim 1, further comprising a polarizing optical element, which is fixed in rotation or rotatable with regard to its polarization direction, positioned in the detection beam path between the beam splitter and the detector.

5. The ophthalmological laser system, according to claim 1, wherein the laser is adjustable to emit, in addition to the illumination laser power, a surgical therapy laser power.

6. An ophthalmological laser system, for the purpose of a surgical follow-up treatment of a cornea, comprising:
a femtosecond laser, emitting radiation that is focusable in an examination region as illumination light via an illumination beam path, the illumination beam path including a scanner unit, and focusing optics;
a beam splitter in the illumination beam path that directs radiation, which reaches the beam splitter from the direction of an examination region to a detector as detection light through a confocal aperture diaphragm, and a control unit programmed to execute the following:
irradiating of the cornea positioned in the examination region by the laser at an illumination laser power and mapping of detection light by the detector, wherein the control unit causes scanning of the cornea three-dimensionally through irradiating said cornea on several points and mapping detection light; and
identifying of an existing laser incision in the cornea from a previous femtosecond laser treatment and determination of form, position or both form and position of the existing laser incision by analysis of the detection light;
wherein the laser is adjustable to emit, in addition to the illumination laser power, a surgical therapy laser power wherein the control unit is further programmed to execute the following, after determining at least one of the form, structure, and position of the laser incision:
determining of irradiation control data for a refractive surgical follow-up treatment, wherein the control unit takes into account the determined form, position or both form and position of the laser incision; and
irradiating the cornea with a surgical therapy laser power in accordance with the determined irradiation control data.

7. The ophthalmological laser system, according to claim 1, wherein the control unit is further programmed to execute:
immobilizing an eye, containing the cornea, before the irradiation with illumination laser power by application of an immobilization device, and
after the determination of the form, position or both form and position of the laser incisions or after a surgical therapy, releasing the immobilization of the eye.

8. The ophthalmological laser system, according to claim 1, further comprising a lock-in amplifier for the detector that is coupled with the laser.

9. A computer implemented method of operating an ophthalmological laser system, the laser of which is switchable between an illumination laser power and a therapy laser power, and the laser light of which is focusable three-dimensionally in a variable fashion in a cornea, comprising:
immobilizing an eye containing the cornea by application of an immobilization device;
irradiating the cornea, positioned in an examination region, by the laser with the illumination laser power;
scanning the cornea three dimensionally by irradiating the cornea at several scan points;
mapping detection light by means of a detector;
identifying an existing laser incision in the cornea from a previous femtosecond laser treatment;
determining form, position or both the form and the position of the laser incision by analysis of the detection light at the scan points;
determining irradiation control data for a refractive surgical follow-up treatment taking into account the determined form and/or position of the laser incisions;
irradiating the cornea by the laser with the surgical therapy laser power in accordance with the determined irradiation control data; and
releasing the immobilization of the eye.

10. The method, according to claim 9, further comprising scanning such that two consecutive scan points differ from each other in all three spatial coordinates.

11. The method, according to claim 9 further comprising adjusting a pulse frequency of the laser light, in dependence of the speed of the scan movement of a focal point of the laser beam relative to the cornea.

12. The method according to claim 9, further comprising executing the step of irradiating and scanning the cornea several times along a scan curve, wherein the scan curve is utilized during each scan cycle in a varyingly offset position, varyingly rotated position or both the varyingly offset position and the varyingly rotated position.

13. The method, according to claim 9, further comprising subtracting a darkfield value from the mapped detection light.

14. A computer readable data storage medium, comprising instructions that cause a computer operably coupled to an ophthalmological laser system, the laser of which is switchable between an illumination laser power and a therapy laser power, and the laser light of which is focusable three-dimensionally in a variable fashion in a cornea to perform a method, the instructions comprising:
immobilizing an eye containing the cornea by application of an immobilization device;
irradiating the cornea, positioned in an examination region, by the laser with the illumination laser power;
scanning the cornea three dimensionally by irradiating the cornea at several scan points;
mapping detection light by means of a detector;
identifying an existing laser incision in the cornea from a previous femtosecond laser treatment;
determining form, position or both the form and the position of the laser incision by analysis of the detection light at the scan points;

determining irradiation control data for a refractive surgical follow-up treatment taking into account the determined form, position or form and position of the laser incision;

irradiating the cornea by the laser with the surgical therapy laser power in accordance with the determined irradiation control data; and releasing the immobilization of the eye.

15. The computer readable data storage medium as claimed in claim 14, the instructions further comprising scanning such that two consecutive scan points differ from each other in all three spatial coordinates.

16. The computer readable data storage medium as claimed in claim 14, the instructions further comprising adjusting a pulse frequency of the laser light, in dependence of the speed of the scan movement of a focal point of the laser beam relative to the cornea.

17. The computer readable data storage medium as claimed in claim 14, the instructions further comprising executing the step of irradiating and scanning the cornea several times along a scan curve, wherein the scan curve is utilized during each scan cycle in a varyingly offset and/or varyingly rotated position.

18. The computer readable data storage medium as claimed in claim 14, the instructions further comprising subtracting a darkfield value from the mapped detection light.

19. The ophthalmological laser system, according to claim 6, wherein the beam splitter is a polarization beam splitter, which selectively decouples the detection light onto the detector such that the detection light exhibits a polarization direction different from the illumination light.

20. The ophthalmological laser system, according to claim 6, further comprising an optical phase retardation system positioned in the illumination beam path between the focusing optics and the examination region such that the illumination light passing through the optical phase retardation system is given a polarization direction which corresponds with the decoupled detection light.

21. The ophthalmological laser system, according to claim 6, further comprising a polarizing optical element, which is fixed in rotation or rotatable with regard to its polarization direction, positioned in the detection beam path between the beam splitter and the detector.

\* \* \* \* \*